United States Patent [19]

Urban

[11] Patent Number: 4,720,461
[45] Date of Patent: Jan. 19, 1988

[54] SUCCINATE-SENSITIVE, NODULATION-ENHANCING RHIZOBIUM MUTANTS FOR USE WITH LEGUMES

[75] Inventor: James E. Urban, Manhattan, Kans.

[73] Assignee: Kansas State University Research Foundation, Manhattan, Kans.

[21] Appl. No.: 905,280

[22] Filed: Sep. 8, 1986

[51] Int. Cl.$^4$ .............................................. C12N 1/20
[52] U.S. Cl. ................................ 435/253; 435/172.1; 435/878; 71/6
[58] Field of Search ............... 71/6, 7, 8; 435/878, 435/172.1, 245, 253

[56] References Cited

FOREIGN PATENT DOCUMENTS

| 2469861 | 6/1981 | France | 435/878 |
| 163690 | 2/1986 | Japan | 435/878 |

OTHER PUBLICATIONS

Urban (1979), Appl. Environ, Microbiol., 38:1173–1178.
Urban and Dazzo (1982), Appl. Environ. Microbiol. 44:219–226.
Ronson et al. (1981), Proc. Natl. Acad. Sci. U.S.A. 78:4284–4288.
Glenn and Brewin (1981), J. Gen. Microbiol., 126:237–241.
Gardiol (1982), J. Bacteriol. 151:1621–1623.

*Primary Examiner*—Ferris H. Lander
*Attorney, Agent, or Firm*—Tilton, Fallon, Lungmus & Chestnut

[57] ABSTRACT

Nodulation-enhancing mutants of Rhizobium species are prepared by growing a wild-type strain in a medium as the only carbon source at a sub-minimum concentration for normal growth, the mutant cells thus obtained are further selected by comparative nodulation to obtain mutants which produce two to three times as many nodules as the corresponding wild-type strain.

8 Claims, No Drawings

SUCCINATE-SENSITIVE, NODULATION-ENHANCING RHIZOBIUM MUTANTS FOR USE WITH LEGUMES

FIELD OF INVENTION

The field of this invention is Rhizobium for use with legume crops to form nitrogen-fixing root nodules. The invention is particularly concerned with Rhizobium mutants which provide enhanced nodulation.

BACKGROUND OF INVENTION

The symbiotic relationship between legume crops and Rhizobium bacteria is well-known. Within the genus, Rhizobium are relatively specific as symbionts for particular legume crops. For example, *Rhizobium trifolii* is specific in nodulating clover, *Rhizobium japonicum* for soybeans, etc. However, all of the Rhizobium share a common morphology and characterization as nodulating bacteria for legume crops.

The nodulation mechanisms associated with rhizobia have been extensively studied but are still not fully understood. In soil in which certain crops are grown, such as soybeans, the symbiotic Rhizobium becomes indigenous. If the required Rhizobium is not present in the soil or is there in inadequate amounts, the practice has been to add the selected Rhizobium to the soil, either directly or in admixture with the seeds of the particular legume crop.

Cells of the rhizobia are attracted to the roots of the legume, become attached thereto, and undergo a transformation to a form known as "bacteroids". During the transformation, the rhizobial cells stop dividing and swell to a greatly enlarged size. It is known that the presence of succinate in sufficient concentration can induce swelling of rhizobial cells corresponding to the initial step in forming bacteroids. In 1979 I reported experiments with *Rhizobium trifolii* wherein succinate induced swelling of the cells to a large, pleomorphic non-dividing form similar to that of bacteroids. Urban (1979) *Appl. Environ. Microbiol.* 38: 1173-1178. Later experiments showed that a critically high concentration of succinate (viz. 16.6 mM) was inductive for cell swelling of *R. trifolii* and bacteroid-type transformation. Urban and Dazzo (1982), *Appl. Environ. Microbiol.* 44: 219-226. These findings suggested that succinate might be involved in the transformation of vegetative rhizobia to the bacteroid morphology of nitrogen-fixing nodules.

Very little has been published with respect to rhizobial mutants. It has been reported that certain *R. trifolii* mutant strains are incapable of transporting or incorporating $C_4$-dicarboxylates (including succinate). *R. leguminosarum* mutant strains having decreased ability to incorporate succinate tend to form ineffective nodules. Ronson et al. (1981), *Proc. Natl. Acad. Sci. U.S.A.* 78: 4284-4288; and Glenn and Brewin (1981), *J. Gen. Microbiol.* 126: 237-241. It has also been reported that succinate dehydrogenase-deficient mutant strains of *R. meliloti* form ineffective nodules, whereas revertants, like the wild-type strain, form effective nodules on alfalfa. Gardiol (1982) *J. Bacteriol.* 151: 1621-1623.

SUMMARY OF INVENTION

This invention provides new kinds of Rhizobium mutants which can be described generically as succinate-sensitive, nodulation-enhancing mutants. The succinate sensitivity can be described not as a deficiency in the utilization of succinate, but rather as the ability of the mutant to grow normally at lower succinate concentrations than the corresponding wild-type in a medium containing succinate as the sole carbon source.

In connection with the experimental work leading to the present invention, I discovered that a class of rhizobial mutants can be induced to grow normally at suboptimal succinate concentrations; and that some Rhizobium mutants growing at lower succinate concentrations are capable of inducing nodule formation on a host legume on the order of two to three times that obtained with the corresponding wild-type of the particular mutant strain. No Rhizobium mutants have heretofore been reported which provide such enhanced nodulation.

In producing the mutants of this invention, a strain of the wild-type species is tested for growth in a minimal medium containing succinate as the only carbon and energy source, using a series of growth tests with successively lower concentrations. In this way an approximate minimum succinate concentration for normal growth of the wild strain is determined. Substantially lower succinate concentration, such as 50% of the minimal growth concentration, is then used for the initial selection of mutant cells. This reduced-succinate selection procedure may be used with either spontaneous or induced mutations. The mutants selected are those which grow normally at the suboptimal growth concentration.

Further selection of the mutants is made by a plant nodulation test procedure. The nodulating effectiveness of the mutant is compared with the wild-type against the host plant for the species. Those mutants which on the average produce at least twice as many nodules as the wild strain comprise a class of Rhizobium mutants within the broad scope of the present invention. In preferred embodiments, mutants are selected which provide enhanced nodulation of the order of three times that of the wild strain.

DETAILED DESCRIPTION

The mutants of the present invention and their method of production are believed to extend to all species of the genus Rhizobia utilizable with legume crops. Commercially, the more important species are those which are effective for nodulating large scale crops, such as soybeans. The scope of the invention has been demonstrated with reference to *R. trifolii*, which nodulates many varieties of clover, *R. japonicum*, which nodulates soybeans, *R. meliloti*, which nodulates alfalfa, and *R. phaseoli*, which nodulates pole beans. These species are representative and are not limiting. The invention can also be practiced with other rhizobia species, including particularly, *Rhizobium meliloti*, which nodulates alfalfa and other grass crops, and *Rhizobium leguminosarum*, which nodulates several varieties of peas and vetches, as well as rhizobia species for other legumes.

In practicing the method of this invention, a wild-type strain of a Rhizobium is selected for mutation purposes. In its initial form, the strain will exhibit normal growth for the species and will have no unusual sensitivity for succinate. The wild-type strain is cultured in a minimal growth medium containing succinate as the only carbon source at varying succinate concentrations. The lowest succinate concentration at which the wild-type strain exhibits normal growth is determined. The wild-type strain is then further cultured in the minimal medium under conditions of spontaneous or induced mutation at a succinate concentration substantially lower than the concentration determined for the minimal concentration determined for normal growth of the corresponding wild-type strain. For example, a concentration one-half of the minimal concentration may be used. Mutant cells are selected which grow normally at the lower succinate concentration.

The selected mutants are then further tested for nodulation effectiveness. A legume host for the species is grown in soil containing the mutant and also in soil containing the same concentration of the wild-type strain. Finally, mutants which demonstrate an ability to form on the average at least twice as many nodules as the wild-type are chosen. In preferred embodiments, as so far determined, the selected mutants provide increased nodulation of the order of about three times that of the wild species.

A representative mutant has been deposited with the American Type Culture Collection, 12301 Parklawn Drive, Rockville, Md., 20852, being *Rhizobium japonicum* Mutant Strain 15, deposited under ATCC Accession No. 53531. This mutant was prepared from normal wild-type strain of the species by the procedures described above. The morphology of this mutant corresponds with that of the species, except that the mutant is capable of normal growth at lower succinate concentrations and it provides more effective nodulation of its host plant (soybeans for *R. japonicum*). The deposited mutant exhibited enhanced nodulation of the order of three times that of the corresponding wild-type species. The subnormal succinate concentration used for the selection of the *R. japonicum* mutant was 0.8 mM succinate. These concentrations were approximately one-half of the minimum normal growth concentration for the corresponding wild strain.

For this initial selection, a suitable minimum growth medium is used, such as the one described by Bishop et al. (1976), *Plant Physiology* 57: 542–546. Succinate as sodium succinate is substituted for the glycerol and glutamate as the only carbon source in the medium and NH$_4$Cl is added to 5 mM as a source of nitrogen. Other non-toxic water-soluble salts of succinic acid can be used.

The method of preparing the mutants of this invention and the properties of mutants produced thereby are further illustrated by the following examples.

EXAMPLE I

As demonstrated in Urban (1979) and Urban and Dazzo (1982), above cited, succinate at 16.6 mM added to *R. trifolii* in a minimal medium containing another carbon source causes such cells to stop dividing and to swell like bacteroids in clover nodules. Cells in minimal medium with only succinate available as a carbon source are more tolerant of succinate, but even with succinate supplying carbons and energy, 16.6 mM succinate interferes with growth. As a consequence, determination of the minimum concentration of succinate allowing "typical" growth involved evaluation of levels of succinate below 16.6 mM.

The rationale for evaluation of different succinate levels is guided by the fact that bacteria respond to carbon and energy sources such that any level of that source that allows for growth to occur tends to support the maximum amount of growth possible for the given source. A series of approximately 1:2 dilutions pf succinate was prepared. Succinate, at a maximum concentration of 4 mM and ranging down to 0.002 mM, was contained in Bishop et al (1976) medium devoid of sodium glutamate (an organic nitrogen source which I replaced with 5 mM NH$_4$Cl) and containing no other carbon and energy source. The individual succinate concentrations were provided in individual 10 cm diameter Petri dishes of agar-solidified medium. Replicate plates were inoculated by uniformly distributing about 10,000 *R. trifolii* cells over the medium surface, and after seven (7) or more days incubation the amount of growth on each plate was evaluated. Typical results were as follows:

| mM Succinate in Agar | Growth observations |
| --- | --- |
| 4 | good growth, uniform across plate |
| 1.6 | amount of growth slightly less than on 4 mM succinate, but colonies still appear optimum size, uniform across plate |
| 0.8 | growth similar to 1.6 mM succinate |
| 0.4 | much less growth than on 0.8 mM succinate, growth uniform across plate but colonies much smaller than optimum |
| 0.2 | about one-half of growth on 0.4 mM succinate |
| 0.02 | barely visible growth, not uniform |
| 0.002 | barely visible growth, fewer colonies, not uniform |

There were no individual colonies that were perceptably larger than background on any of the succinate concentrations.

The pattern of growth described above indicated that 0.4 mM succinate was a concentration that would not support normal growth of wild type, and therefore should reveal the presence of any mutant *R. trifolii* cells that showed an ability to grow at suboptimal succinate levels, thereby permitting "succinate-sensitive" mutants to be selected.

In the selection of mutants, *R. trifolii* cells growing in Bishop et al. (1976), cited above, minimal medium containing 0.2% mannitol were collected at a cell density of about $1.0 \times 10^9$ cells/ml. The cells were centrifuged, resuspended in minimal medium free of carbon and nitrogen, recentrifuged, and finally resuspended in minimal medium free of carbon and nitrogen. One-tenth ml aliquots ($1.0 \times 10^8$ cells) of the washed cells were spread on each of several hundred Bishop et al. (1976) minimal agar plates with sodium glutamate replaced with 5 mM ammonium chloride and containing 0.4 mM succinate. The 0.1 ml aliquots were spread evenly over the surface of each 10 cm petri plate, and the plates inverted and incubated at 30 degrees C. After 7–10 days incubation any visible colonies were picked and streaked for isolation on fresh medium identical to that used in the initial isolation. Typically, one colony clearly larger than the background growth appeared about once per each ten (10) inoculated plates. A succession of nine (9) additional subcultures involving picking of a typical colony and streaking for isolation on a fresh agar plate was performed after which stock slants were prepared on the same type of medium used in isolation and subculture. Only one subculture, or any number of subcultures between 1 and 9, would have sufficed, as determined by experiment repeats. Stock slants were used to produce working cultures for nodulation assays, etc., and after nodulation assays were run, 3X cultures were mixed in a 1:1 ration with sterile glycerin and frozen at −20° C.

The initial plating on 0.4 mM succinate provided a selective environment which permitted any bacterium which had experienced a spontaneously-arising mutation to produce progeny and grow into a visible colony.

Nodulation assays were conducted with the selected succinate-sensitive mutants as follows. Seeds of dutch white clover (Henry Field Seed and Nursery Co., Shenandoah, IA) were surface sterilized by 3 minute exposure to 1% (w/v) fresh NaOCl (laundry bleach) and rinsed with sterile distilled water. Sets of 3 seeds were placed on the surface of 6 ml "Fahraeus" nitrogen-free plant nutrient medium (cited below) solidified with 0.75% (w/v) Bacto Agar (Difco) and contained in a $18 \times 150$ mm culture tube. Tubes and agar were sterilized and cooled immediately before addition of seeds. Three replicates for each mutant to be assayed were prepared. After 2 days in the dark at 30° C. seedlings were about 1 cm in height.

The 2-day-old seedlings were inoculated with about $5 \times 10^7$ of the respective succinate sensitive mutants. Inoculum cells were washed from the surface of the 0.4 mM succinate plate used for the 9th subculture as described in the paragraph immediately above. Tubes containing inoculated seedlings were covered with Saran Wrap (Dow Chemical Co.) and maintained aseptically. Plants were grown under a 16 hour light, 8 hour dark, regimen at a temperature of 26° C. Nodules were counted at 30, 61, and 110 days after seedling inoculation. Nodule counts at 110 days were essentially identical to counts at 61 days.

Comparisons of mutant efficacy were made by comparing the number of nodules per plant produced by mutants at the 61 day count. In all cases the average number of nodules produced per plant (sum of nodules on each of the three plants (repeated measures) in each of the tree tubes (replicates)/sum of plants in the three tubes (normally 9 plants)) was compared to the average number of nodules produced by wild-type (the stock *R. trifolii*) from which the succinate-sensitive mutants were isolated. The formula for Fahraeus medium was based on Fahraeus, G., 1957, J. Gen. Microbiol. 16: 374–381).

The final selection of the spontaneous *R. trifolii* succinate-sensitive mutants included four mutant strains of similar nodulating characteristics. All of the selected strains providing increased nodulation of the order of three times that of the wild-type strain from which the mutants were prepared.

EXAMPLE II

Following a similar procedure to that of Example I, succinate-sensitive nodulation-enhancing strains of *Rhizobium japonicum* were prepared. Instead of relying on spontaneous mutation, which is relatively time consuming, mutation of the wild strain was accelerated by the use of a transposon. The transposon used in induction of succinate-sensitive *Rhizobium japonicum* was Tn5. The transposon was borne on one of two plasmids, each of which was harbored in a different strain of *Escherichia coli*. The strain designation of one of the transposon donors is *E. coli* thy- threo- leu- SM10/pSUP1011 km$^r$ Ch.$^r$. The other transposon donor is *E. coli* his- arg- (Lac del) 2492/pJB4JI Km$^r$Gm$^r$. The recipient (parent) strain was *R. japonicum* USDA 110.

Succinate-sensitive, transposon-induced mutants were selected via the following procedure. Penassay broth (Difco Detroit, MI) was inoculated with the desired donor strain and incubated with aeration at 37° C. After donor cells had reached a population density of $1 \times 10^8$ cells/ml, cells were refrigerated for subsequent use as donors. In actual transposon transfers, 20.0 ml of *R. japonicum* USDA 110 (grown in Bishop et al. (1976) minimal-mannitol medium to a cell density of $2 \times 10^8$ cells/ml) were mixed with 2.0 ml of desired donor. The mixed cells were centrifuged and the cell pellet resuspended in 5.0 ml of enriched medium (Bishop et al. (1976) minimal-mannitol plus 0.2% Difco Yeast Extract and 0.2% Difco Proteose Peptone.)

After four (4) hours incubation at 30° C., the donor/recipient mix was again centrifuged and the cell pellet resuspended in 2.0 ml of Bishop et al. (1976) minimal medium (devoid of mannitol). The plasmid was transferred from donor to recipient during the preceding 4 hours incubation and upon plasmid transfer, or very soon thereafter, the transposon left its location in the plasmid and entered the genetic material of the recipient, causing mutations. To select for mutants that were succinate-sensitive, one-tenth ml ($>1 \times 10^9$ cells/ml) of the resuspended cell pellet was evenly spread on the surface of 10 cm Petri dishes containing agar-solidified Bishop et al. (1976) minimal medium devoid of sodium glutamate and containing 0.8 mM succinate. Also present in the selective medium was the antibiotic Kanamycin, at a concentrtion of 3 to 8 ug/ml. For *R. japonicum* 0.8 mM is the suboptimal succinate concentration as determined by the assay method described for *R. trifolii* in Example I above. Kanamycin provides an environment in which only transposon-containing, succinate-sensitive cells can survive, and rules out the selection of spontaneously-arising mutants. Kanamycin concentrations were purposely kept at the minimal level that would prevent transposon-free wild-type from growing on the selective medium, and variation in concentrations in the range of 3–8 ug/ml were apparently a function of antibiotic freshness. Appropriate controls consisted of spreading correspondingly washed and concentrated donor or receipient cells to plates of the same selective medium. No colonies were expected or tolerated on control plates, but plates spread with recombinant mixtures tended to contain about one recombinant colony per plate. If colonies appeared on any control plates, the experiment of the moment was abandoned and no recombinant plates used. Recombinant colonies (clones of succinate-sensitive mutants) were picked and subcultured on the same medium after which agar-slant stocks were prepared. Agar-slants consisted of the same medium as that on which recombinants were selected).

Nodulation assays were conducted essentially as described in Example I above except that seeds were soybeans (Williams, 82) and only two (2) seeds (repeated measures) per vessel (replicate) were used. Also rather than using agar-solidified medium, 150 ml vermiculite in a $140 \times 60$ mm glass jar with a mouth of 30 mm diameter and a volume of 250 ml was substituted. Vermiculite was wetted with about 100 ml Fahraeus medium [see Example I above] and jars with damp vermiculite were sterilized and cooled immediately before seed addition. Seedlings were inoculated two days after seed sterilization, and nodule number was quantitated 30 days after seedling inoculation. Soybean plants were removed from vermiculite for quantitation of nodules 30 days after seed inoculation.

A variation of the nodulation assay was run in which case each succinate-sensitive mutant was added to soybean seedlings in combination with suspensions of wild type at a ratio of 10 mutants/1 wild type and 1 mutant/1 wild type. The mixed inoculations were designed to test how well the mutants compete with wild type and the results show comparably enhanced nodulation by succinate-sensitive mutants even with mutants in the presence of equal number of wild type cells. Mutants were able to induce 3X the nodule number of wild type cells.

The finally selected mutant strains of R. japonicum obtained exhibited 3X nodulation. Strain 15, which is representative, was deposited with the ATCC, as described above, under ATCC No. 53531.

EXAMPLE III

R. meliloti and R. phaseoli transposon-induced mutants were generated in a fashion essentially identical to that described for R. japonicum in Example II. The only significant difference between methodology for either of the two species from the R. japonicum procedure was the concentration of succinate found to be suboptimal. The succinate concentration used to select for succinate-sensitive R. meliloti was 0.66 mM and the concentration used for R. phaseoli was 0.08 mM. Kanamycin levels in the succinate-minimal selection medium was also 3-8 μg/ml.

Nodulation will be evaluated as in Examples I and/or II, using alfalfa for testing the R. meliloti mutants and polebeans for using the R. phaseoli mutants. Finally, selected mutants will have enhanced nodulation of at least 2X and preferably about 3X with reference to that obtained with the corresponding wild-type strains that were used to produce the mutants.

For commercial production of the succinate-sensitive nodulation-enhancing mutants produced as described above, large scale propagation procedures may be used. For example, to grow increased amounts of succinate sensitive cells as might be needed to produce commercial inoculants, the following procedure should be used: From agar-slant minimal medium containing the appropriate sub-optimal mutant(s), cells are transferred to non-selective enriched medium, i.e., minimal-(mannitol) medium plus 2% yeast extract and 2% proteose peptone, at a cell density giving visible turbidity ($>1\times10^6$ cells/ml). Several divisions in the enriched medium will yield maximum population densities and produce cells which induce nodules readily.

I claim:

1. A viable culture of a succinate-sensitive, nodulation-enhancing strain of Rhizobium, comprising a mutant of a Rhizobium species exhibiting normal growth in a minimal growth medium containing succinate as the only carbon source at a succinate concentration below the minimum concentration permitting normal growth of the wild-type species of the mutant, said mutant strain inducing an average formation of at least two times as many nodules on a legume host plant for the species as the wild-type species.

2. The culture of claim 1 in which said Rhizobium species is R. japonicum.

3. A viable culture of succinate-sensitive, nodulation-enhancing strain of Rhizobium, comprising a mutant of a Rhizobium species exhibiting normal growth in a minimal growth medium containing succinate as the only carbon source at a succinate concentration at about one-half the minimum concentration permitting normal growth of the wild-type species corresponding to the mutant, said mutant strain inducing formation of the order of about three times as many nodules on a legume host for the species as said wild-type species.

4. The culture of claim 3 in which said Rhizobium species is R. japonicum.

5. The method of obtaining a succinate-sensitive, nodulation-enhancing, mutant of a Rhizobium species, comprising:
   (a) selecting a wild-type strain of a Rhizobium species for mutation, said strain exhibiting normal growth for the species;
   (b) culturing said wild-type strain in a minimal growth medium containing succinate as the only carbon source at varying succinate concentrations and determining the lowest succinate concentration at which the wild-type strain exhibits normal growth;
   (c) culturing the wild-type strain in the said medium under conditions of spontaneous or induced mutation at a succinate concentration substantially lower than the concentration determined in step (b);
   (d) selecting mutant cells which grow normally at the lower succinate concentration;
   (e) testing the selected cells for nodulation with a legume host plant for the species in comparison with said wild-type strain; and
   (f) selecting mutant cells which induce an average formation of at least two times as many nodules as the wild-type strain.

6. The method of claim 5 in which said Rhizobium species is R. japonicum.

7. The method of obtaining a succinate-sensitive, nodulation-enhancing mutant of a Rhizobium species, comprising:
   (a) selecting a wild-type strain of a Rhizobia species for mutation, said strain exhibiting normal growth for the species;
   (b) culturing said wild-type strain in a minimal growth medium containing succinate as the only carbon source at varying succinate concentrations and determining the lowest succinate concentration at which the wild-type strain exhibits normal growth;
   (c) culturing the wild-type strain in the said medium under conditions of spontaneous or induced mutation at a succinate concentration of not over one-half of the concentration determined in step (b);
   (d) selecting mutant cells which grow normally at the lower succinate concentration;
   (e) testing the selected cells for nodulation with a legume host plant for the species in comparison with said wild-type strain; and
   (f) selecting mutant cells which induce formation on the order of about three times as many nodules as the wild-type strain.

8. The method of claim 7 in which said Rhizobium species is R. japonicum.

* * * * *